United States Patent
Thalhammer et al.

(10) Patent No.: US 9,354,330 B2
(45) Date of Patent: May 31, 2016

(54) METHOD FOR DETECTING RADIATION AND EXAMINATION DEVICE FOR THE RADIATION-BASED EXAMINATION OF A SAMPLE

(71) Applicants: Helmholtz Zentrum Muenchen Deutsches Forschungszentrum fuer Gesundheit und Umwelt (GmbH), Neuherberg (DE); Technische Universitaet Muenchen, Munich (DE)

(72) Inventors: Stefan Thalhammer, Munich (DE); Markus Hofstetter, Neubiberg (DE); John Howgate, Munich (DE); Martin Stutzmann, Erding (DE)

(73) Assignees: Helmholtz Zentrum Muenchen Deutsches Forschungszentrum fuer Gesundheit und Umwelt (GmbH), Neuherberg (DE); Technische Universitaet Muenchen, Munich (DE)

( * ) Notice: Subject to any disclaimer, the term of this patent is extended or adjusted under 35 U.S.C. 154(b) by 106 days.

(21) Appl. No.: 14/381,982

(22) PCT Filed: Feb. 15, 2013

(86) PCT No.: PCT/EP2013/000454
§ 371 (c)(1),
(2) Date: Aug. 28, 2014

(87) PCT Pub. No.: WO2013/127496
PCT Pub. Date: Sep. 6, 2013

(65) Prior Publication Data
US 2015/0041662 A1    Feb. 12, 2015

(30) Foreign Application Priority Data

Feb. 29, 2012 (DE) .................... 10 2012 004 087

(51) Int. Cl.
| | | |
|---|---|---|
| *H05G 1/64* | (2006.01) | |
| *G01T 1/24* | (2006.01) | |
| *G01N 23/083* | (2006.01) | |

(52) U.S. Cl.
CPC .............. *G01T 1/24* (2013.01); *G01N 23/083* (2013.01)

(58) Field of Classification Search
CPC ...... G01T 1/24; G01T 1/2928; G01N 23/083; H04N 5/32
USPC .......... 378/98.8; 250/370.01, 370.07, 370.08, 250/370.09
See application file for complete search history.

(56) References Cited

U.S. PATENT DOCUMENTS

| | | |
|---|---|---|
| 7,313,224 B1 | 12/2007 | Saunders |
| 8,729,486 B2 | 5/2014 | Daghighian et al. |
| 2007/0297569 A1 | 12/2007 | Saunders |
| 2012/0025087 A1 | 2/2012 | Daghighian et al. |

FOREIGN PATENT DOCUMENTS

| | | |
|---|---|---|
| DE | 102007026665 A1 | 12/2007 |
| WO | 2010142773 A2 | 12/2010 |
| WO | 2010142773 A3 | 12/2010 |

OTHER PUBLICATIONS

Bataiev et al., "Effect of proton irradiation on AlGaN/AlN/GaN HEMT's", Semiconductor Physics, Quantum Electronics & Optoelectronics, vol. 14, No. 3, pp. 279-286 (2011).
Hofstetter et al., "Development and evaluation of gallium nitride-based thin films for x-ray dosimetry", Phys. Med. Bio., vol. 56, pp. 3215-3231 (2011).
Hofstetter et al., "Real-time x-ray response of biocompatible solution gate AlGaN/GaN high electron mobility transistor device", Applied Physics Letters, vol. 96, pp. 092110-1-3 (2010).
International Search Report for PCT/EP2013/000454 dated May 27, 2013.

Primary Examiner — Courtney Thomas
(74) Attorney, Agent, or Firm — Caesar Rivise, PC

(57) ABSTRACT

A method for detecting radiation during the examination of a sample (1) comprises the steps of generating the radiation, more particularly X-ray radiation or proton radiation, by means of a source device (10), passing the radiation through the sample (1), and detecting the radiation by means of at least one photoelectric solid-state detector (20) containing a photoconduction section having a predetermined response threshold and a potential well section for taking up free charge carriers. The solid-state detector (20) is a GaN- or GaAs-based semiconductor detector and the potential well section contains a two-dimensional electron gas (2DEG). A setting of the radiation is provided in such a way that the solid-state detector (20) is operated separately from the response threshold of the photoconduction section and in a sensitivity range of the potential well section. An examination device (100) is also described, said examination device being configured for an examination of a sample (1) using radiation, more particularly X-ray radiation or proton radiation.

15 Claims, 3 Drawing Sheets

METHOD FOR DETECTING RADIATION AND EXAMINATION DEVICE FOR THE RADIATION-BASED EXAMINATION OF A SAMPLE

BACKGROUND OF THE INVENTION

The invention refers to a method for detecting radiation, e.g. during the investigation of a sample, particularly a method in which radiation generated by means of a source device passes through the sample and is detected by a photoelectric solid-state detector, particularly a method to investigate the sample using radiation, such as X-ray radiation or proton radiation. Furthermore the invention refers to an investigation device which is adapted for the investigation of a sample using radiation, particularly X-ray radiation or proton radiation. Applications of the invention are provided particularly in medical imaging or in the characterisation of materials.

Various techniques are known for the detection of X-ray radiation, which differ in terms of the detectable energy range, the sensitivity, the lifetime and the spatial resolution. For example ionization chambers indicate high sensitivity for the detection of X-ray radiation, but only low local resolution. An improved local resolution is achieved with solid-state detectors, e.g. on the basis of MOSFETs, diamond, diodes and scintillation dosimeters, whilst in these cases disadvantages can arise in terms of the energy range or sensitivity, for example.

A substantial improvement in sensitivity was achieved with detectors based on a GaN/AlGaN heterostructure (see M. Hofstetter et al. in "Applied Physics Letter", vol. 96, 2010, p. 092110). In response to the irradiation with X-ray radiation, charge carriers are generated in the GaN-based detector material. The current which can be measured on the detector is a measure of the received radiation dose.

Previously it was assumed that GaN-based detectors can only be used up to a lower radiation dose limit of a few µGy/s and have insufficient sensitivity for a lower radiation dose.

However interest exists particularly for the purpose of radiation protection to provide solid-state detectors, which combine the advantage of a high local resolution and a high sensitivity at a reduced radiation dose. This interest exists not only in the case of the detection of X-ray radiation, but also for the detection of particle radiation, such as proton radiation.

The objective of the invention is to provide an improved method for detecting radiation, with which disadvantages of conventional methods can be avoided and which is characterised particularly by an improved sensitivity during radiation with a low radiation dose. A further objective of the invention is to provide an improved investigation device for the investigation of a sample using radiation, which avoids disadvantages when operating conventional solid-state detectors and which particularly enables the sample to be exposed to a reduced radiation dose.

These objectives are solved by a method for detecting radiation and an investigation device with the features of the invention.

According to a first aspect of the invention, the above objective is solved by a method for detecting radiation, particularly X-ray radiation or proton radiation, during the radiation-based investigation (analysis, test, particularly imaging) of a sample, in which the radiation is generated with a source device, passes through the sample, and is detected using at least one photoelectric solid-state detector. The solid-state detector includes a single detector element or an array of detector elements. Each detector element is characterised by at least one photoconduction section, which is adapted for a radiation-induced generation of charge carriers, and at least one potential well section, which is adapted for receiving free charge carriers. Each photoconduction section has a response threshold, above which the radiation-induced generation of charge carriers takes place. No measurable charge carriers are generated in the at least one photoconduction section during radiation of the detector element with a radiation dose below the response threshold. According to the invention the radiation is set in such a way that the solid-state detector is irradiated with a radiation dose that is selected separately from the response threshold of each photoconduction section. The radiation is set so that radiation hits the solid-state detector at a radiation dose rate that is below the response threshold of each photoconduction section. According to the invention, the solid-state detector is operated in a sensitivity range of the at least one potential well section.

According to a second aspect of the invention the above objective is solved by an investigation device which is configured for a radiation-based investigation of a sample and which comprises a source device to generate radiation, particularly X-ray radiation or proton radiation, a sample holder to accommodate the sample and a photoelectric solid-state detector with at least one detector element for detecting radiation. The at least one detector element contains at least one photoconduction section with a predetermined response threshold and at least one potential well section for receiving free charge carriers. According to the invention, the investigation device is provided with a setting device which is adapted for setting the radiation in such a way that the at least one detector element is operated separately from the response threshold of the at least one photoconduction section and in a sensitivity range of the at least one potential well section.

The invention is based on the following findings of the inventors. It was established that the signal of the detector element, e.g. on the basis of GaN, is composed of two different partial signals based on different physical phenomena. A first partial signal is generated in the photoconduction section, typically the bulk material of the detector element. A second partial signal is generated in the potential well section, such as a section with a two-dimensional electron gas, in the detector element. It was established by the inventors that the first partial signal disappears with a radiation dose rate below a few µGy/s, particularly below 1 µGy/s, whereas the second partial signal remains measurable at a lower radiation dose rate. The second partial signal is characterised by a relative sensitivity that is comparable to that of the photoconduction section. As special advantage of the invention it was established, however, that only around 0.1% of the number of quanta of radiation, particularly X-ray photons or protons, are required to generate the signal with the potential well section (second partial signal). The advantage is that this surprising result permits samples, particularly biological samples in medical imaging or other radiation-sensitive samples, to be investigated using a substantially reduced radiation dose rate compared to conventional technology. The radiation exposure of the samples is reduced by several orders of magnitude.

A further advantage of the invention lies in the fact that the potential well section in the solid-state detector has a rapid response. The generation of a detector signal and the depletion of the detector signal by charge carriers in the potential well section takes place in a timeframe of less than 10 ms, particularly less than 5 ms. This facilitates a reduction in measuring times, which has a particularly advantageous effect in computed tomography. Tomographic cross-sections can be taken in a shorter time compared to conventional techniques, thereby achieving a further reduction of the radiation exposure of the sample, e.g. a subject under investigation.

The setting of the radiation provided according to the invention includes an influencing of the radiation during its generation and/or transmission to the solid-state detector in such a way that the desired radiation dose rate (radiation dose rate below the response threshold of the photoconduction section) reaches the radiation-sensitive range of the solid-state detector, i.e. the at least one detector element. It is advantageous that different variants of the setting of the radiation are available, which according to the preferred embodiments of the invention can be provided individually or in combination.

According to a first variant, the setting of the radiation can be provided during operation of the source device. The emission intensity of the source device is adjusted so that the desired radiation dose rate hits the solid-state detector. For this purpose the investigation device according to the invention is preferably provided with a source control with which the emission intensity of the source device can be adjusted. The source control can be used, for example, to set a cathode current to generate X-ray radiation in the case of an X-ray tube or an electron current to ionize hydrogen atoms in the case of a proton source. The setting of the emission intensity has the advantage that the source device can be adapted particularly easily to the current investigation conditions.

According to a second variant, the setting of the radiation comprises the setting of a filter device arranged between the source device and the solid-state detector. The filter device is adapted to attenuate the radiation generated by the source device so that the solid-state detector is subjected to the desired radiation dose rate. The filter device includes at least one filter made e.g. from aluminium to set X-ray radiation or e.g. from quartz glass to set proton radiation. The filter device can be arranged at any position on the radiation path between the source device and the solid-state detector. The filter device is particularly preferably arranged between the source device and the sample, however, so that the radiation exposure of the sample can be minimised.

According to a third variant of the invention, the setting of the radiation comprises the setting of a detection distance between the source device and the solid-state detector. By increasing the detection distance, the radiation dose rate on the solid-state detector can be reduced in the case of a source device with which non-collimated radiation is generated. For this purpose the investigation device is preferably provided with a positioning device, with which the detection distance can be adjusted. With the positioning device the position of the solid-state detector can be set relative to the source device and/or the position of the source device relative to the solid-state detector. Particularly preferred is an embodiment of the invention in which the detection distance varies by positioning the source device and is set to the desired value, whilst the distance between the sample and the solid-state detector remains unchanged. The advantage in this case is that the radiation exposure of the sample can be minimised.

The setting of the radiation according to the invention can be undertaken by the practitioner depending on the investigation conditions. The setting of the radiation can be performed in such a way that the solid-state detector is operated in the sensitivity range of the potential well section, in particular depending on the radiation attenuation in the sample and/or under consideration of tabular values, where applicable after a preliminary test to determine the radiation dose rate. It is advantageous for the setting of the radiation to be automatable. According to a preferred embodiment of the invention, a feedback control of the setting of the radiation, particularly the setting of the emission intensity, the filter device and/or the detection distance, can be provided in dependency on a detector signal of the solid-state detector. The setting of the radiation takes place in such a way that the radiation dose rate on the solid-state detector is attenuated such that the detector signal is characteristic for the operation of the solid-state detector in the sensitivity range of the photoconduction section. The investigation device is preferably provided with a control device, with which the setting device, particularly the source control, a filter control of the filter device and/or the positioning device can be controlled in dependency on the detector signal of the solid-state detector.

As an advantage the invention can be realized with different types of solid-state detectors. Particularly preferably the solid-state detector contains at least one semiconductor detector element with a semiconductor heterostructure, in which at least one potential well section is formed. Particularly preferred is a GaN or GaAs-based semiconductor detector element is provided, e.g. on the basis of GaN, GaAlN or GaAs, which is characterised by a heterostructure to form the at least one potential well section. The heterostructure is configured such that the at least one potential well section contains a two-dimensional electron gas (2 DEG), such as that described, for example, in the abovementioned publication by M. Hofstetter et al.

According to a further advantageous embodiment of the invention, the sensitivity of the solid-state detector can be changed by applying an electrical voltage to the at least one potential well section and setting it to a desired value. For this purpose the at least one detector element is preferably provided with an actuation electrode which is arranged with respect to the potential well section such that the charge carrier distribution in the potential well section can be changed on applying voltage to the actuation electrode.

As an advantage the method according to the invention can be implemented once or repeated several times with various geometric arrangements of the source device, the sample and the solid-state detector. According to a particularly preferred application of the invention, the method is used during CT imaging. For this the method according to the invention is repeated with different projected directions of the radiation through the sample, in order to record a number of projected images of the sample and conduct a CT imaging of the sample. In this embodiment of the invention, the investigation device is preferably provided by CT scanners or the investigation device is part of a CT scanner.

BRIEF DESCRIPTION OF THE DRAWINGS

Further advantages and details of the invention are described below, making reference to the attached drawings as follows.

Preferred embodiments of the invention will be described below, with exemplary reference to the investigation of a sample with X-ray radiation and the detection of the X-ray radiation with a GaN-based solid-state detector with a (matrix) array of detector elements each with a photoconduction section and a potential well section. It is emphasised that implementation of the invention is not restricted to the investigation with X-ray radiation, but is also possible with other types of radiation, particularly with proton radiation. Furthermore, a different type of solid-state detector, particularly a semiconductor detector, such as a GaAs-based semiconductor detector, can be used. The detector elements each can have multiple photoconduction sections and/or multiple potential well sections, in which cases the radiation is set such that all detector elements are operated in the sensitivity range of all potential well sections. Although the use of an array of detector elements can be preferred for transmission imaging, the solid-state detector can alternatively have only one single detector element.

The embodiments of the invention are described with reference to the setting of the radiation (attenuation of the radiation) in such a way, that the solid-state detector is irradiated in the sensitivity range of the potential well section, and to a correspondingly configured investigation device. Details of operation of a source device, such as an X-ray source or a proton source, the operation of a solid-state detector, the image acquisition with a number of detector elements and/or CT imaging are not described, because these are known from the state of the art.

Figure 1:
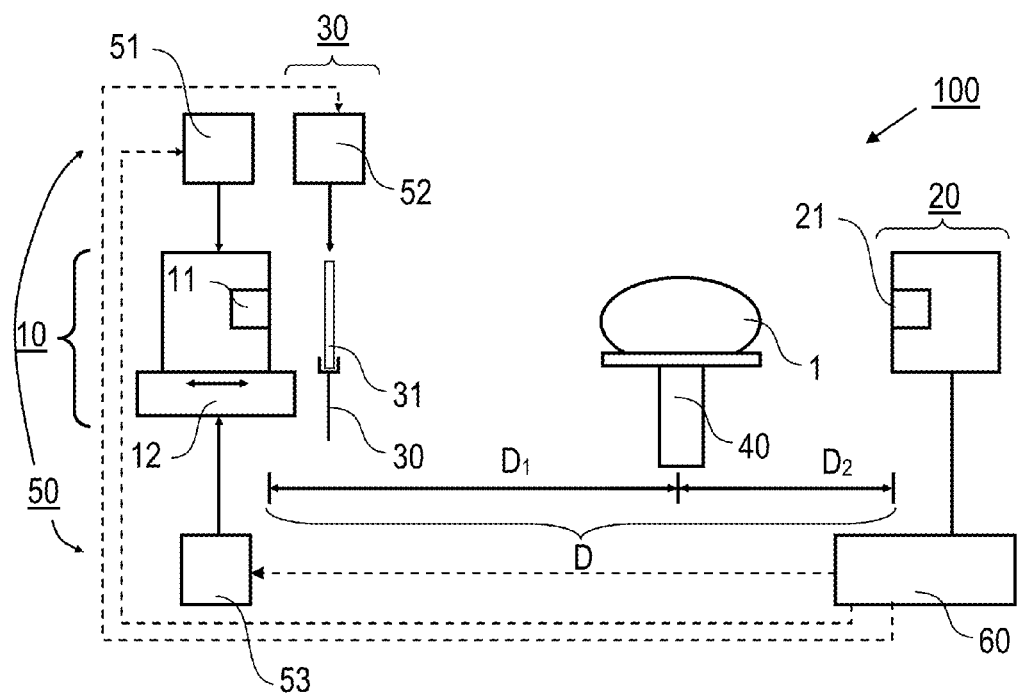
FIG. 1: a diagrammatic illustration of a first embodiment of the investigation device according to the invention.

FIG. 1 illustrates in a diagrammatic view of a first embodiment of an investigation device 100 according to the invention, which is configured for an investigation of a sample 1 using X-ray radiation, and for this has a source device 10, a sample holder 40 and a photoelectric solid-state detector 20. The source device 10 comprises an X-ray tube 11, which is arranged on an adjustable source carrier 12, e.g. a carriage-rail combination. The solid-state detector 20 includes an array of detector elements 21, which are typically all of the same type. The sample holder 40 is arranged along the radiation path between the source device 10 and the solid-state detector 20 such that the sample 1 placed on the sample holder 40 is penetrated by radiation during operation of the investigation device 100 and the X-ray radiation hits onto the array of detector elements 21.

The distance D between the X-ray tube 11 and the array of detector elements 21 is made up of the distance between the source and sample $D_1$ and the distance between the sample and detector $D_2$. With the source carrier 12, the detection distance D is adjustable, e.g. in a range of 10 cm to 5 m. The distance between the sample and detector $D_2$ is preferably fixed, whilst the distance between the source and sample $D_1$ is changed.

FIG. 1 further illustrates the provision of a diagrammatically illustrated filter device 30, which is arranged in the radiation path between the X-ray tube 11 and the sample 1. The filter device 30 comprises e.g. an aluminium filter 31. Although in FIG. 1 a distance is shown between the X-ray tube 11 and the filter device 30, in practice it may be an advantage if the filter device 30 is firmly connected to the source device 10 and e.g. can be moved with this where necessary (see FIG. 2).

The investigation device 100 according to the invention is provided with a setting device 50, with which the X-ray radiation can be set, and particularly attenuated, so that the detector elements 21 are operated in a sensitivity range of the potential well sections of the detector elements 21. Different variants of the setting device 50 are shown collectively in FIG. 1, and which comprises a source control 51, a filter control 52 of the filter device 30 and a positioning device 53. It is not compulsory for the specified measures for setting the radiation to be provided collectively. Alternatively only one of the source control 51, filter control 52 and positioning device 53 or combinations of these can be provided.

The source control 51 is a control circuit, using which the cathode current of the X-ray tube 11 can be adjusted. The source control 51 can be provided as a separate control circuit or be integrated in the source device 10. The filter control 52 is a drive with which various filters 31, which differ according to their attenuating factors, are shifted into the radiation path. The positioning device 53 is a further control circuit, with which the source carrier 12 can be operated. The positioning device 53 can likewise be provided as separate control circuit or can be integrated in the source device 10.

In the represented embodiment of the invention, the investigation device 100 is provided with a control device 60, with which the components of the setting device 50 can be regulated in dependency on a detector signal from one of the detector elements 21 of the solid-state detector 20. The control device 60 compares the detector signal of the solid-state detector with a predetermined radiation dose rate reference value. Furthermore the control device 60 emits a control signal to the source control 51, the filter control 52 and/or the positioning device 53, until by adjusting the emission intensity, the filter and/or the detection distance D, the detector signal represents a radiation dose rate below the desired reference value. This feedback control can be conducted continuously during operation of the investigation device 100 or in a preliminary test in which the sample 1 is provided on the sample holder 40. The provision of the control device 60 is not absolutely essential. Alternatively the cathode current of X-ray tube 11, the detection distance and/or the filter 31 can be set manually.

The investigation of the sample 1 with investigation device 100 takes place in such a way that X-ray radiation is generated with the source device 10, and directed through the filter 31 and the sample 1 to the solid-state detector 20. The X-ray radiation passes through sample 1 and is thereby attenuated. The radiation which has passed through the sample is captured with spatial resolution by the solid-state detector. The detector signal of each detector element of the solid-state detector is characteristic for the number of charge carriers which are generated in the potential well section of the detector element 21. The detector signals of the solid-state detector 20 are then evaluated and subjected to an image reconstruction procedure, for example, to obtain a projected image of sample 1.

Figure 2:
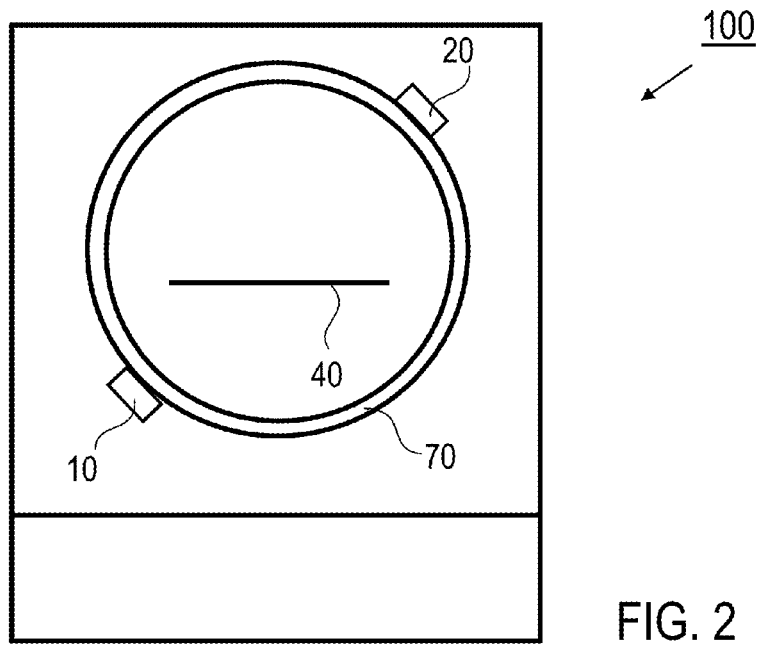
FIG. 2: a diagrammatic illustration of a further embodiment of the investigation device according to the invention.

The investigation of sample 1 can be repeated, in which various projected directions are set for reconstruction of a CT image. For this the second embodiment of the investigation device 100 according to the invention according to FIG. 2 is preferably used. In this case the investigation device 100 is a CT scanner (illustrated diagrammatically in FIG. 2), with a combination of a source device 10 and a solid-state detector 20, which has a rotary arrangement in a gantry 70 around the sample holder 40. Depending on the type of CT scanner, the solid-state detector 20 includes one single detector element or an array of detector elements. In this embodiment of the invention, the detection distance is constant, so that the setting of the cathode current of the X-ray tube in the source device 10 and/or the setting of a filter (not shown) on source device 10 is provided to set the X-ray radiation. The investigation of sample 1 on sample holder 40 takes place as known from conventional operation of CT scanners, whereas the X-ray radiation is set so that the solid-state detector 20 is operated in the sensitivity range of the at least one potential well section.

Figure 3:
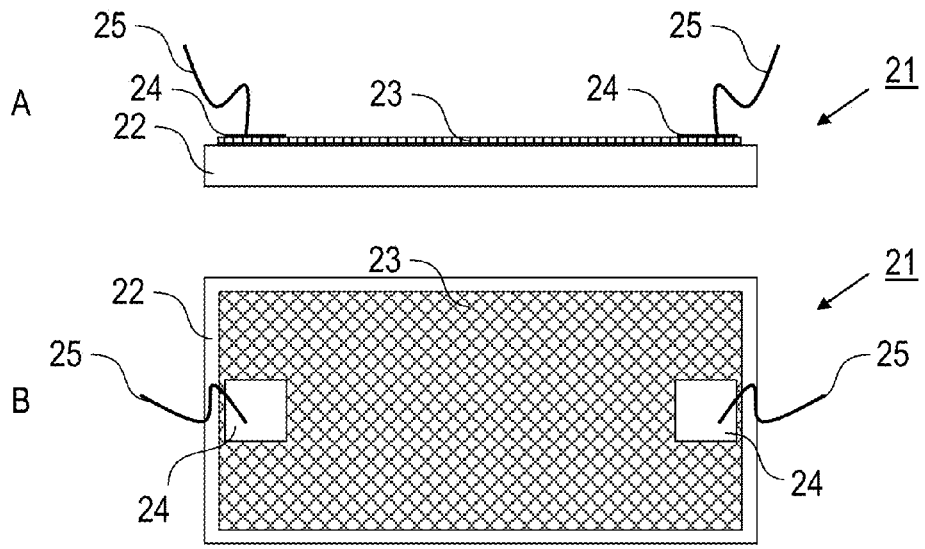
FIG. 3: a diagrammatic illustration of a detector element used according to the invention.

FIG. 3 illustrates diagrammatically an example of a detector element 21 for detecting the X-ray radiation in diagrammatical sectional view (FIG. 3A) and in diagrammatical top view (FIG. 3B). The detector element 21 contains a carrier substrate 22, a detector layer 23 and contact electrodes 24, which are connected via connecting lines 25 to an electronic circuit for current measurement (not shown). The carrier substrate 22 comprises e.g. sapphire with a thickness of 0.33 mm. The detector layer 23 is a GaN—AlGaN heterostructure, as described e.g. in the abovementioned publication by M. Hofstetter et al. The detector layer 23 contains a layer structure with a photoconduction section and a potential well section for taking up free charge carriers. The contact electrodes 24, which are also indicated as source and drain electrodes, consist e.g. of Ti—Al. Preferably the contact electrodes have the same width as the detector layer. They are applied by means of thermal vapor deposition or electron beam vapor deposition on the detector layer 23. The dimensions of the detector layer 23 (FIG. 3B) are e.g. 0.5 mm·2 mm, whilst the dimensions of the contact electrodes 24 are for example 500 µm·500 µm, respectively. The detector element 21 is sensitive to X-ray radiation which is generated with an X-ray tube with a voltage in the range 20 kV to 300 kV.

Figure 4:
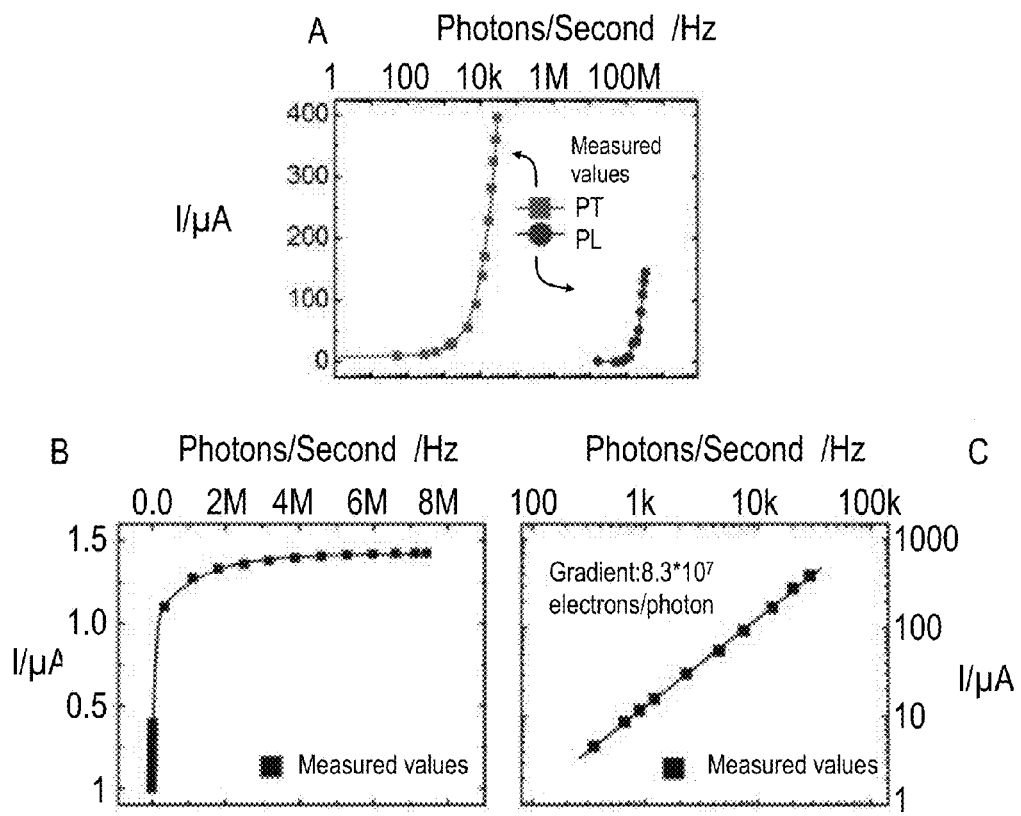
FIG. 4: representation of curves on graphs showing experimental results obtained using the method according to the invention.

FIG. 4 illustrates experimental results which have been determined when irradiating a detector element 21 according to FIG. 3. FIG. 4A shows the detector current I, which was measured during measurements with spatial resolution in the photoconduction section PL ("off channel") and in the potential well section ("on channel"). In the case of a photon flow below around 1 million photons per second, the charge carriers contributing to the detector signal are generated only in the potential well section, where a two-dimensional electron gas is formed. In FIG. 4B the detector current I measured in the potential well section is shown in a range of a higher photon flow. With falling photon flow, the number of charge carriers generated in the potential well section of the detector layer 23 falls drastically, and the detector current I decreases accordingly. In the lower range of the photon flow (FIG. 4C), a linear sensitivity curve of the potential well section is seen. The inventors have found that a linear relationship exists between the detector current and the dose rate in the dose rate range, in which only negligible charge carriers are generated in the photoconduction section and where the charge carriers generated in the potential well section form the detector signal. According to the invention, the detection of the X-ray radiation takes place in the dose rate range shown in FIGS. 4B and 4C, so that on the one hand the radiation exposure of the sample is minimised and on the other hand a reproducibly analysable signal with high sensitivity is measured.

Figure 5:
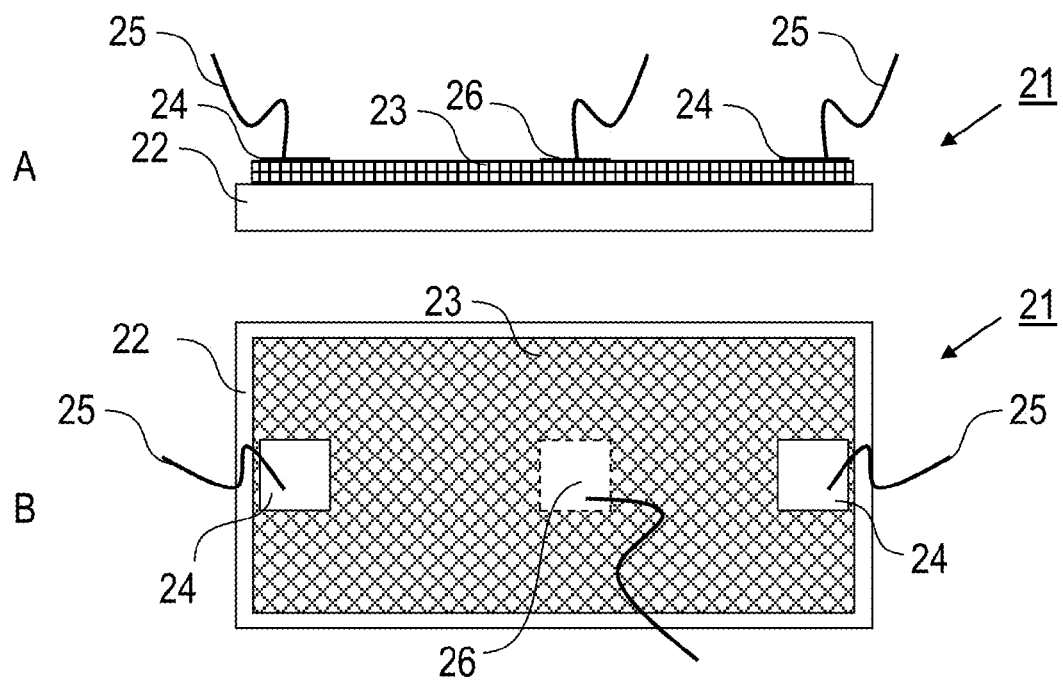
FIG. 5: a diagrammatic illustration of a further detector element used according to the invention.

FIG. 5 illustrates a modified variant of a detector element 21 used according to the invention, which is essentially structured like the detector element 21 according to FIG. 3 and is additionally provided with an actuation electrode 26, which is also indicated as gate electrode. When an electric current is supplied to the actuation electrode 26, an electrical potential is applied on the potential well section in the detector layer 23, which influences the sensitivity of the detector element 21.

Figure 6:
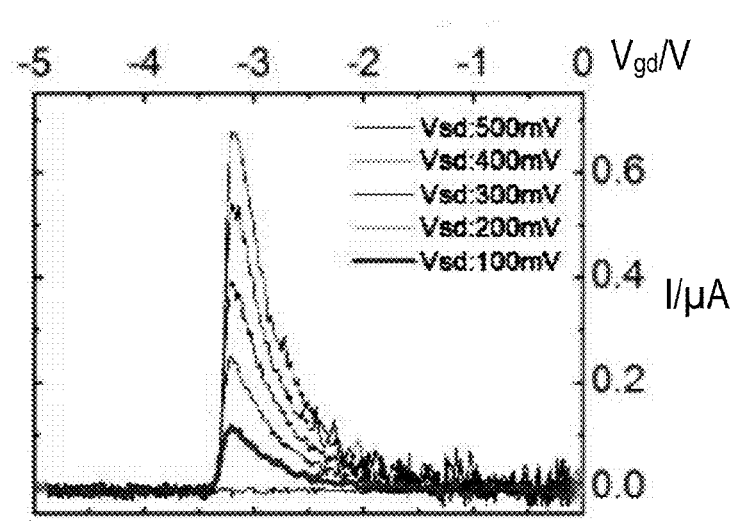
FIG. 6: representation of curves on a graph showing further experimental results obtained using the detector element in accordance with FIG. 5.

FIG. 6 illustrates how the detector current I is generated in the case of a fixed dose rate (e.g. $10^5$ protons/sec) subject to the voltage $V_{gd}$ between the actuation electrode 26 and one of the electrodes 24 with different voltages $V_{sd}$ between the electrodes 24. With increasing voltage on the actuation electrode 26, an increase can be seen in the detector current I and with this an increase in sensitivity.

The features of the invention disclosed in the above description, the drawings and the claims can be of importance individually and also in combination for the realization of the invention in its different embodiments.

The invention claimed is:

1. A method for detecting radiation during an investigation of a sample, comprising the following steps:
  (a) generation of the radiation with a source device;
  (b) passing of the radiation through the sample;
  (c) detection of the radiation using at least one photoelectric solid-state detector, which includes a photoconduction section with a predetermined response threshold and a potential well section for receiving free charge carriers, wherein the solid-state detector is a GaN or GaAs-based semiconductor detector and the potential well section contains a two-dimensional electron gas; and
  (d) setting of the radiation in such a way that the solid-state detector is operated separately from the response threshold of the photoconduction section and in a sensitivity range of the potential well section.

2. The method in accordance with claim 1, wherein step (d) comprises at least one of the following:
  (d1) setting of an emission intensity of the source device;
  (d2) setting of a filter device, which is arranged between the source device and the solid-state detector; and
  (d3) setting of a detection distance between the source device and the solid-state detector.

3. The method in accordance with claim 2, wherein step (d2) comprises setting the filter device, which is arranged between the source device and the sample.

4. The method in accordance with claim 2, wherein step (d3) comprises setting the detection distance, which is arranged between the source device and the sample.

5. The method in accordance with claim 2, wherein at least one of the setting of the emission intensity, the setting of the filter device and the setting of the detection distance is feedback-controlled in dependency on a detector signal of the solid-state detector.

6. The method in accordance with claim 1, further comprising the step of setting a sensitivity of the solid-state detector by applying an electrical potential to the potential well section.

7. The method in accordance with claim 1, wherein steps (a) to (c) are repeated with different projected directions of the radiation through the sample and a computed tomography imaging of the sample is conducted.

8. The method in accordance with claim 1, wherein the radiation comprises X-ray radiation or proton radiation.

9. An investigation device, which is configured for an investigation of a sample using radiation, comprising:
  a source device, which is adapted to generate the radiation;
  a sample holder to accommodate the sample;
  a photoelectric solid-state detector, which is adapted to detect the radiation and includes a photoconduction section with a predetermined response threshold and a potential well section for receiving free charge carriers, wherein the photoelectric solid-state detector is a GaN or GaAs-based semiconductor detector and the potential well section contains a two-dimensional electron gas; and
  a setting device, which is configured to set the radiation in such a way that the solid-state detector is operated separately from the response threshold of the photoconduction section and in a sensitivity range of the potential well section.

10. The investigation device in accordance with claim 9, wherein the setting device comprises at least one of the following:
- a source control being adapted for adjusting an emission intensity of the source device;
- a filter device, which is arranged between the source device and the solid-state detector; and
- a positioning device being adapted for setting a detection distance between the source device and the solid-state detector.

11. The investigation device in accordance with claim 10, wherein the filter device is arranged between the source device and the sample.

12. The investigation device in accordance with claim 10, wherein the positioning device is adapted for setting the detection distance between the source device and the sample.

13. The investigation device in accordance with claim 9, wherein a control device is provided, with which the control device can be feedback-controlled in dependency on a detector signal from the solid-state detector.

14. The investigation device in accordance with claim 9, wherein the solid-state detector has an actuation electrode, which is connected to the potential well section and which is adapted for setting a sensitivity of the solid-state detector by applying an electrical potential to the potential well section.

15. The investigation device in accordance with claim 9, which is configured for investigating the sample using X-ray radiation or proton radiation.

* * * * *